(12) United States Patent
Basaraba et al.

(10) Patent No.: US 8,268,330 B2
(45) Date of Patent: Sep. 18, 2012

(54) HYPOXIA INDUCIBLE FACTOR INDUCER AND METHODS FOR USING THE SAME

(75) Inventors: Randall Joseph Basaraba, Fort Collins, CO (US); Helle Bielefeldt-Ohmann, Brisbane (AU)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 12/532,138

(22) PCT Filed: Mar. 19, 2008

(86) PCT No.: PCT/US2008/057440
§ 371 (c)(1), (2), (4) Date: Sep. 18, 2009

(87) PCT Pub. No.: WO2008/115959
PCT Pub. Date: Sep. 25, 2008

(65) Prior Publication Data
US 2010/0112004 A1   May 6, 2010

Related U.S. Application Data

(60) Provisional application No. 60/919,058, filed on Mar. 19, 2007.

(51) Int. Cl.
*A61K 39/04* (2006.01)
(52) U.S. Cl. ............... 424/248.1; 424/184.1; 424/234.1
(58) Field of Classification Search ............... None
See application file for complete search history.

(56) References Cited

U.S. PATENT DOCUMENTS 6,821,751 B2   11/2004   Goldberg et al.

OTHER PUBLICATIONS

Yeruva et al (Clin Vaccine Immunol. Oct. 2006; 13: 1137-1142).*
Quadri et al 1998 Chemistry and Biology, vol. 5, pp. 631-645.*
Hantke et al 2003, PNAS, 100 (7) 3677-3682).*
Orme, Vaccine 24:2-19, 2006.*
Girard et al, Vaccine 23:5725-5731, 2005.*
Chong, T.W., et al. "A mycobacterial iron chelator, desferri-exochelin, induces hypoxia-inducible factors 1 and 2, NIP3, and vascular endothelial growth factor in cancer cell lines." Cancer Res. Dec. 1, 2002;62(23):6924-7.
Woo, K.J., et al. "Desferrioxamine, an iron chelator, enhances HIF-1alpha accumulation via cyclooxygenase-2 signaling pathway." Biochem Biophys Res Commun. Apr. 28, 2006;343(1):8-14. Epub Feb. 28, 2006.
Roy, A., et al. "Activation of HIF-1alpha mRNA by hypoxia and iron chelator in isolated rat carotid body." Neurosci Lett. Jun. 17, 2004;363(3):229-32.
Macham, L.P., et al. "Extracellular iron acquisition by mycobacteria: role of the exochelins and evidence against the participation of mycobactin." Infect Immun. Dec. 1975;12(6):1242-51.
Zhou, Y.D., et al. "Hypoxia-inducible factor-1 activation by (-)-epicatechin gallate: potential adverse effects of cancer chemoprevention with high-dose green tea extracts." J Nat Prod. Dec. 2004;67(12):2063-9.
Ratledge, C., et al. "The occurrence of carboxymycobactin, the siderophore of pathogenic mycobacteria, as a second extracellular siderophore in *Mycobacterium smegmatis*." Microbiology. Aug. 1996;142 ( Pt 8):2207-12.
Bauerfeind, R., et al. "Molecular characterization of *Mycobacterium paratuberculosis* isolates from sheep, goats, and cattle by hybridization with a DNA probe to insertion element IS900." J Clin Microbiol. Jul. 1996;34(7)1617-21.
Thorel, M.F., et al. "Numerical taxonomy of mycobactin-dependent mycobacteria, emended description of *Mycobacterium avium*, and description of *Mycobacterium avium* subsp. *avium* subsp. nov., *Mycobacterium avium* subsp. *Paratuberculosis* subsp. nov., and *Mycobacterium avium* subsp. *silvaticum* subsp. nov." Int J Syst Bacteriol. Jul. 1990;40(3):254-60.

* cited by examiner

*Primary Examiner* — Padma Baskar
(74) *Attorney, Agent, or Firm* — Dann, Dorfman, Herrell & Skillman; Kathleen D. Rigaut

(57) ABSTRACT

The present invention provides vaccine compositions and methods for using the same. Generally, the vaccine is used to prevent infection of a microorganism that produces an HIF inducing compound. Accordingly, vaccines of the invention comprise at least a portion of an HIF inducing compound that is produced by the microorganism.

11 Claims, No Drawings

HYPOXIA INDUCIBLE FACTOR INDUCER AND METHODS FOR USING THE SAME

CROSS-REFERENCE TO RELATED APPLICATIONS

This application claims the priority benefit of U.S. Provisional Application No. 60/919,058, filed Mar. 19, 2007, which is incorporated herein by reference in its entirety.

STATEMENT REGARDING FEDERALLY FUNDED RESEARCH

The U.S. Government has a paid-up license in this invention and the right in limited circumstances to require the patent owner to license others on reasonable terms as provided for by the terms of Grant No. AI054697 awarded by the National Institutes of Health.

FIELD OF THE INVENTION

The present invention relates to vaccine compositions and methods for using the same. Generally, the vaccine is used to prevent infection of a microorganism that produces mammalian transcription factors hypoxia inducing factor 1 and 2 (HIF) inducing compounds. Accordingly, vaccines of the invention comprise at least a portion of an HIF inducing compound that is produced by the microorganism.

BACKGROUND OF THE INVENTION

Traditionally, vaccines have been based on live attenuated, or inactivated microorganisms. However, in many instances these strategies are inefficient due to factors such as antigenic variability of microorganisms such as bacteria or fungi. Peptide vaccines that consist of antigenic peptides or peptide fragments of microorganisms have been developed. Conserved peptide fragments are less likely to exhibit antigenic variability, and can overcome some of the problems associated with traditional peptides. Accordingly, subunit vaccines have been developed that target conserved regions of microorganisms. However, synthetic peptide vaccines tend to be poorly immunogenic, and also tend to induce humoral antibody responses, but are less able to induce cell-mediated responses.

With the emergence of drug resistant and/or virulent strains of microorganisms, there is a need for a more effective vaccine against a wide variety of infectious microorganisms.

SUMMARY OF THE INVENTION

Generally, the invention provides vaccines for a microorganism (i.e., microbe) and methods for using the same. In some aspects, vaccines for microorganisms that produce HIF inducing compound is provided. Typically, the vaccine comprises at least a portion of an HIF inducing compound that is produced by the microorganism, a precursor of the HIF inducing compound, or a combination thereof.

In some embodiments, the microorganism is a bacteria. The vaccine can also include one or more siderophores or bacterial product that is capable of binding or chelating one or more metal cations. Exemplary metal cations include iron, copper, magnesium, zinc, manganese, and nickel. Exemplary siderophores include, but are not limited to, Mycobacterial spp. siderophores mycobactin, carboxymycobactin, and exochelins.

In some embodiments, the microorganism is any bacteria that produce similar chelators or siderophores.

Still in other embodiments, the microorganism is *Mycobacterium tuberculosis*, or related mycobacteria or other members of the Actinobacteria, including, but not limited to, pathogenic and non-pathogenic *Mycobacterium* spp.

Exemplary HIF inducing compounds include, but are not limited to, siderophores, or iron chelators, such as mycobactin, carboxymycobactin and exochelins disclosed above.

In some embodiments, the siderophore comprises mycobactin, carboxymycobactin, exochelins, or a combination thereof.

Yet in other embodiments, the vaccine comprises a fragment of the HIF inducing compound. In particular, those fragments that are recognized by the immune system of the subject.

The vaccine can also include an epitope of the microorganism to elicit immune response from the subject.

In some embodiments, the vaccine includes an attenuated or inactivated microorganism. Alternatively, the vaccine can include any conventional compositions known to one skilled in the art. For example, a vaccine composition for *M. tuberculosis* can be BCG-vaccine which includes an HIF inducing compound such as those disclosed herein.

Other aspects of the invention provide a method for vaccinating a subject against a microorganism infection. Such methods generally comprises administering to the subject a vaccine composition comprising at least a portion of an HIF inducing compound that is produced by the microorganism, a precursor of the HIF inducing compound, or a combination thereof.

In some embodiments, the vaccine includes an epitope of the microorganism.

In other embodiments, the vaccine includes an attenuated or inactivated microorganism.

Methods of the invention are applicable for vaccinating against a wide variety of microorganism including various bacteria or fungi. Generally, methods of the invention are suited for vaccinating a subject against a microorganism that produces an HIF inducing compound. In some embodiments, the microorganism is a bacteria. Within these embodiments, in some instances, the microorganism is *Mycobacterium tuberculosis*, other pathogenic and non-pathogenic mycobacterium spp. or other members of the Actinobacteria family.

In some embodiments, the HIF inducing compound is a siderophore or a cation chelator, for example, mycobactin, carboxymycobactin or exochelins. Within these embodiments, in some instances, the siderophore comprises mycobactin, carboxymycobactin, exochelins, or a combination thereof.

Yet in other embodiments, the vaccine comprises a fragment of the HIF inducing compound.

Still other aspects of the invention provide a method for stimulating an immune response against *Mycobacterium tuberculosis* in a subject. Such methods generally include administering a composition comprising mycobactin, carboxymycobactin, exochelins, a fragment thereof, or a combination thereof to the subject.

In some embodiments, the composition includes and epitope of *Mycobacterium tuberculosis*.

Still in other embodiments, the composition includes an attenuated or inactivated *Mycobacterium tuberculosis*.

Yet in some embodiments, the composition includes those of BCG vaccine.

DETAILED DESCRIPTION OF THE INVENTION

While various approaches have been developed to produce different vaccine formulations for microorganisms (i.e., microbes), most conventional vaccines elicit immune response using the microorganism itself (typically in inactive or attenuated form) or an epitope of the microorganism's outer membrane or protein. However, in many instances these strategies are inefficient due to factors such as antigenic variability of microorganisms. Synthetic peptide (e.g., epitope) vaccines that are sometimes used often do not elicit sufficient immune response, and in many cases tend to induce humoral antibody responses, but are less able to induce cell-mediated responses.

The growth and virulence of many microorganism (e.g., bacteria and fungi such as *Mycobacterium tuberculosis, Escherichia coli, Salmonella, Streptomyces pilosus, Yersinia pestis, Vibrio cholerae*, etc.) depend on their ability to scavenge or obtain host iron, an essential and limited nutrient in vivo. Some aspects of the invention provide a vaccine that comprises a microorganism's iron carrier, e.g., siderophore and methods for using the same to elicit an immune response from a subject.

Siderophores

A siderophore (Greek for iron carrier) is an iron chelating compound secreted by microorganisms. Ferric ions ($Fe^{3+}$) have a very low solubility at neutral pH and therefore generally cannot be utilized by microorganisms. Siderophores dissolve these ions by chelation as soluble $Fe^{3+}$ complexes that can be taken up by active transport mechanisms of microorganisms. Many siderophores are nonribosomal peptides.

Under anoxic conditions, iron is generally in the +2 oxidation state (ferrous) and soluble. However, under oxic conditions, iron is generally in the +3 oxidation state (ferric) and forms various insoluble minerals. To obtain iron from such minerals, microorganisms produce iron-binding siderophores that bind iron and transport it into the microorganism. One exemplary group of siderophores consists of derivatives of hydroxamic acid, which chelate ferric iron very strongly. Examples of other siderophores produced by various bacteria and fungi include, but are not limited to, ferrichrome (*Ustilago sphaerogena*), enterobactin (*Escherichia coli*), mycobactin (*Mycobacterium*), enterobactin and bacillibactin (*Bacillus subtilis*), ferrioxamine B (*Streptomyces pilosus*), fusarinine C (*Fusarium roseum*), yersiniabactin (*Yersinia pestis*), vibriobactin (*Vibrio cholerae*), azotobactin (*Azotobacter vinelandii*), pseudobactin (*Pseudomonas* B 10), erythrobactin (*Saccharopolyspora erythraea*) and ornibactin (*Burkholderia cepacia*).

Pseudomonads

Like all aerobic bacteria, *pseudomonads* need to take up iron via the secretion of siderophores which complex iron (III) with high affinity. Much progress has been made in the elucidation of siderophore-mediated high-affinity iron uptake by *Pseudomonas*, especially in the case of the opportunistic pathogen, *P. aeruginosa*. Fluorescent *pseudomonads* produce the high-affinity peptidic siderophore pyoverdine, but also, in many cases, a second siderophore of lesser affinity for iron. Some of the genes for the biosynthesis and uptake of these siderophores have been identified and the functions of the encoded proteins known. Iron uptake via siderophores is regulated at several levels, via the general iron-sensitive repressor Fur (Ferric Uptake Regulator), via extracytoplasmic sigma factors/anti-sigma factors or via other regulators. Since *pseudomonads* are ubiquitous microorganisms, it is not surprising to find in their genome a large number of genes encoding receptors for the uptake of heterologous ferrisiderophores or heme reflecting their great adaptability to diverse iron sources.

Mycobacterium

Among mycobacteria, important pathogens for animals and men are found. For example, *Mycobacterium tuberculosis* causes tuberculosis, *Mycobacterium leprae* is responsible for leprosy, and *Mycobacterium avium* and *Mycobacterium intracelulare* also cause tuberculosis in immunodepressed patients as well as other mycobacteria which cause other diseases in humans, although to a lesser degree. In the case of animals, *Mycobacterium avium* subsp. pararatuberculosis causes Jones Disease in ruminants and *Mycobacterium bovis* causes tuberculosis in cattle highlight.

Tuberculosis (TB) is one of the more dangerous mycobacterial diseases in men. It constitutes a world health problem and it is the leading cause of death associated to infectious diseases despite vaccination with BCG and the use of a great number of drugs for its control. It is estimated that the third part of the world population has been infected by *Mycobacterium tuberculosis*. All over the world, it is estimated that eight million people develop active TB every year and three million dies. Co-infection with the Human Immunodeficiency Virus (HIV) represents 3 to 5% of the cases. Due to the great spread of the disease, new and better diagnosis methods, vaccine preparations and therapeutic agents are required.

Currently, the appearance of *M. tuberculosis* strains with resistance to multiple drugs is an increasing problem which claims the development of new therapeutic alternatives for the high number of infected individuals (50 millions) and for the increasing number of patients with these characteristics occurring in the future. Additionally, there exist multiple species of mycobacteria causing diseases in man for which an adequate treatment is not available.

BCG is the only tuberculosis vaccine currently available for human use. Almost three billion doses have been applied all over the world. Its efficacy widely varies depending on the strain used, nutritional status, genetic background, aging and presence of intercurrent infections. Its use is considered only effective to prevent the serious forms of the disease (miliary and meningitis) in infancy but not to prevent pulmonary tuberculosis. Therefore, there is a need to develop new vaccine preparations.

One of the most important conventional strategies to develop vaccines against tuberculosis include the use of inactivated strains, genetically or not attenuated strains, nucleic acids vaccines, subunits vaccines and attenuated live strains expressing antigens of *M. tuberculosis*.

As stated above, *Mycobacterium tuberculosis* (*M. tuberculosis*), the causative agent of human tuberculosis, is an intracellular pathogen that is spread primarily between individuals by aerosolized respiratory secretions. The initial foci of mixed inflammation that develop in the lung following aerosol exposure are called primary lesions. A clinical and pathologic feature that characterizes primary lesions is that in both lung and draining lymph nodes, granulomas often become calcified and appear on chest radiographs as discrete mineralized densities. The importance of primary lesions is that they represent foci of irreversible tissue damage that can persist for the life of the patient and in some cases, may harbor small numbers of viable but dormant bacilli that may serve as the source of reactivation tuberculosis during times of lowered host resistance. While well organized or calcified granulomas may prevent bacilli from spreading from the initial site of infection, they also represent a functional or mechanical barrier to both immune effector cells and penetration by sterilizing concentrations of anti-tuberculosis drugs.

The present inventors have discovered that ferric iron accumulates both intra- and extra-cellularly in the primary lung lesions of subjects infected with the H37Rv strain of *Mycobacterium tuberculosis*. Iron accumulated within the cytoplasm of macrophages at the periphery of the primary granulomatous lesions while extra-cellular ferric iron accumulated in the central necrotic areas. The deposition of extra-cellular ferric iron within necrotic foci coincided with the accumulation of calcium and phosphorus in the form of dystrophic calcification. Chemical analysis of isolated primary lesions demonstrated that in addition to iron, calcium and phosphorus, the lesions contained magnesium, copper and zinc. The accumulation of iron within macrophages corresponded to an increased expression of intra-cellular heavy chain (H) ferritin and the expression of surface receptors for transferrin. The expression of macrophage H ferritin paralleled the presence or absence of necrosis within primary lesions. Macrophages in primary lung lesions from subjects vaccinated with *Mycobacterium bovis* BCG* (BCG) prior to experimental infection had reduced macrophage transferrin receptor and intra-cellular H ferritin expression. BCG vaccination ameliorated extra-cellular ferric iron accumulation as well as necrosis, and dystrophic calcification. Without being bound by any theory, it is believed that these data show that BCG vaccination ameliorates necrosis and dystrophic mineralization as well as iron accumulation in part by down-regulating the expression of macrophage transferrin receptors and H ferritin in vivo.

Hypoxia-Inducible Factors

Hypoxia-inducible factors (HIFs) are transcription factors that respond to changes in available oxygen in the cellular environment, in particular, to decreases in oxygen, or hypoxia. Most, if not all, oxygen-breathing species express the highly-conserved transcriptional complex HIF-1, which is typically a heterodimer composed of an α- and a β-subunit, the latter being a constituitively-expressed aryl hydrocarbon receptor nuclear translocator (ARNT). HIF-1 belongs to the PER-ARNT-SIM (PAS) subfamily of the basic-helix-loop-helix (bHLH) family of transcription factors. Overexpression of a natural antisense transcript (aHIF) of this gene is associated with nonpapillary renal carcinomas.

The α-subunit of HIF-1 (i.e., HIF-1α) is a target for prolyl hydroxylation by HIF prolyl-hydroxylase, which makes HIF-1α a target for degradation by the E3 ubiquitin ligase complex, leading to quick degradation by the proteasome. This occurs in normoxic conditions. In hypoxic conditions, HIF prolyl-hydroxylase is typically inhibited, since it utilizes oxygen as a cosubstrate.

In some instances, hypoxia results in a buildup of succinate, due to inhibition of the electron transport chain in the mitochondria. The buildup of succinate further inhibits HIF prolyl-hydroxylase action, since it is an end-product of HIF hydroxylation. In a similar manner, inhibition of electron transfer in the succinate dehydrogenase complex due to mutations in the SDHB or SDHD genes can cause a build-up of succinate that inhibits HIF prolyl-hydroxylase, stabilizing HIF-1α. This is termed pseudohypoxia.

HIF-1, when stabilized by hypoxic conditions, upregulates several genes to promote survival in low-oxygen conditions. These include glycolysis enzymes, which allow ATP synthesis in an oxygen-independent manner, and vascular endothelial growth factor (VEGF), which promotes angiogenesis. HIF-1 acts by binding to HIF-responsive elements (HREs) in promoters that contain the sequence NCGTG.

In general, HIFs are important to development. In mammals, deletion of the HIF-1 genes typically results in perinatal death. HIF-1 has been shown to be important to chondrocyte survival, allowing the cells to adapt to low-oxygen conditions within the growth plates of bones.

Hypoxia is a common feature of many cancers. It contributes to local and systemic tumor progression as well as potentially compromising radiotherapy and chemotherapy. HIF-1 is an important component in changing the transcriptional response of tumors under hypoxia. It targets the transcription of over 60 genes involved in many aspects of cancer biology including cell survival, glucose metabolism, cell invasion and angiogenesis. Over-expression of HIF-1 has been associated with increased patient mortality in several cancer types including breast, stomach, cervical, endometrial and ovarian cancers. The pharmacological manipulation of HIF-1 has marked effects on tumor growth, and it could prove to be an important target for drug therapy, both in cancer and in other hypoxia-dependent disease states.

HIF-1α (or basic helix-loop-helix transcription factor) is a human gene. The protein encoded by HIF-1 is a bHLH-PAS transcription factor found in mammalian cells growing at low oxygen concentrations. It plays an essential role in cellular and systemic responses to hypoxia. This is one of the class of hypoxia inducible factors, a family that includes Hif1a, Hif2a, and Hif3a.

HIF is expressed by cells in either inflammatory or cancer lesions when cells are deprived of oxygen. In some microorganism infections, HIF expression is induced by either cytokines or by the activity of microorganism's iron chelators (e.g., mycobactin or other siderophores). The iron chelation pathway is believed to be independent of local tissue oxygen, hence perceived hypoxia, and is related to the iron chelating activity of siderophores (e.g., mycobactin and carboxymycobactin). In some microorgansims, e.g., *Mycobacterium tuberculosis*, infection HIF expression is induced early in the course of infection via the iron scavenging activity of the bacterial siderophore and yields the condition that is referred herein as perceived hypoxia. Often perceived hypoxia is detected in the infection by elevated levels of HIF prior to tissue damage.

The present inventors have discovered that siderophores, such as mycobactin, activates hypoxia inducible factor (HIF-1α, Heme oxygenase (HO), interleukin 8 (IL-8), and/or TGF-β) in cells infected with TB. IL-8 and TGF-β are cytokines with important inflammatory properties that contribute to the hallmark tuberculosis lesions in both animals and humans. HIF is a transcription factor that is able to regulate the activity of many genes. Furthermore, the present inventors have discovered that HIF-1α, HO, and vascular endothelial growth factor (VEGF), expressions are associated with tuberculosis. HIF expression has been identified early in the course of disease before there is oxygen deprivation in tissues, i.e., actual hypoxia, which would lead to damaged tissues and the eventual hallmark conditions of TB—dystrophic calcification.

Perceived Hypoxia in Lesions from *M. Tuberculosis* Infected Guinea Pigs

The present inventors have discovered that both actual and perceived hypoxia occur in the pathogenesis of tuberculosis. The concept of perceived hypoxia is based on the fact that essentially all cells when exposed to a hypoxic microenvironment express the oxygen sensing protein HIF. Besides being exposed to hypoxia, HIF expression can be induced by stabilizing HIF by iron chelating. While actual hypoxia is believed to occur in the chronic stages of infection associated with chronic pulmonary and extra-pulmonary inflammation, perceived hypoxia is believed to occur in the acute or subacute stages before extensive tissue damages occurs. The present inventors have discovered that antibodies against human HIF-1α cross reacts with the guinea pig protein. Using this antibody, the present inventors have found expression of HIF-1α in lung and lymph node in some cases as early as 5 days post-infection and specific nuclear expression indicative of functional nuclear translocation. Both cytoplasmic and nuclear expression increases with the progression of disease. In addition, the present inventors have discovered that at least one of the down-stream products of HIF-1α transcription regulation, heme-oxygenase 1 (HO-1) is also expressed in lesions of subjects infected with *M. tuberculosis*.

Mycobactin Induction of HIF-1α in Macrophages in Vitro

The present inventors have discovered that *M. tuberculosis* derived mycobactin and the iron-chelator desferroxamine in a dose dependent manner induce accumulation of cytoplasmic HIF-1α followed by nuclear translocation in a subset of the cells. Actual hypoxia is defined as a reduction of tissue oxygen concentration below physiologically normal levels despite adequate perfusion of the tissue by blood. Actual hypoxemia is also defined as deficient oxygenation of blood such as occurs in anemic hypoxia where the oxygen carrying capacity of the blood is reduced as a result of reduced concentration or function of the iron containing protein, e.g., hemoglobin. It is believed that localized tissue hypoxia occurs at sites of inflammation and particularly when inflammation is destructive, sometimes resulting in tissue necrosis that involves the local blood supply. There are likely multiple causes of localized and systemic hypoxia. Macrophages and granulocytes that infiltrate sites of inflammation must undergo special adaptations to perform phagocytic and bactericidal functions in a localized hypoxic microenvironment. One such adaptation is believed to be the oxygen-dependant expression of the host transcription factor hypoxia inducible factor 1 (HIF-1). It is believed that HIF-1α is expressed by essentially all cells of the body and has been shown to regulate target genes associated with important biological functions such as glycolysis, erythropoiesis, angiogenesis and vascular remodeling. Without being bound by any theory, it is believed that HIF-1 regulates bactericidal capacity of phagocytes through maintenance of ATP pools and regulation of pro-inflammatory responses.

While oxygen-dependant (actual hypoxia) regulation of HIF-1α occurs under actual hypoxic conditions, HIF-1α can be regulated by signals other than hypoxia including, nitric oxide (NO), cytokines, growth factors, cobalt chloride and iron chelators (perceived hypoxia). Iron chelators such as desferrioxamine also stabilize HIF-1α by sequestration and reduction of the labile cytoplasmic iron pool.

The iron chelating activity of *M. tuberculosis* siderophores, e.g., mycobactin and carboxymycobactin, induces HIF-1α in infected macrophages in a non-oxygen dependent fashion during the acute infection. Early primary lesions of tuberculosis in some subjects express HIF-1α in vivo. It has been shown that in mouse model of tuberculosis, lesions fail to develop hypoxia yet have an increase in HIF-1α gene expression. Therefore the expression of HIF-1α by *M. tuberculosis* infected mouse macrophages in the absence of actual hypoxia, indicates nonoxygen-dependant mechanisms of HIF-1α expression associated with *M. tuberculosis* infection.

Like in humans, the morphogenesis of primary lesions in guinea pigs infected with *M. tuberculosis* progresses from small foci of mixed inflammation to lesions that develop central necrosis and dystrophic calcification. Vaccination of guinea pigs with *Mycobacterium bovis* BCG (BCG) prior to aerosol infection results in delayed development of primary lesions that are generally smaller and rarely develop necrosis and dystrophic calcification. The morphologic differences between the primary lesions from BCG-vaccinated and non-vaccinated guinea pigs serves as a good model for human and can be used to study the mechanisms of action of BCG and the progression and pathogenesis of the primary lesions of tuberculosis.

Dystrophic calcification is a pathologic process that involves the intra- and extra-cellular precipitation of calcium phosphate in areas of tissue necrosis. The hydroxyapatite mineral complex that forms is similar to that found in bones and teeth and develops following initiation (or nucleation) and progresses by a process referred to as propagation. The initiation of intra-cellular calcification occurs with the influx of calcium within mitochondria of dead or dying cells, whereas extra-cellular phospholipid vesicles from cytoplasmic membranes or organelles of dying cells can serve as the nidus for extra-cellular calcification. In some instances, extra-cellular but not intra-cellular iron has been shown to serve as an initiator of dystrophic calcification.

Iron is a micronutrient required by essentially all living organisms, since it is structurally incorporated into a wide variety of proteins that are crucial for normal metabolic processes, including cell respiration, growth and DNA synthesis. Macrophages throughout the body play an important role in iron metabolism through the ability to store and release iron at times of excess and deficiency, respectively. Through protein binding, iron is rendered non-toxic and the in vivo availability to infectious pathogens is limited. Non-protein bound or free iron is toxic causing cytotoxicity through the formation of reactive oxygen species and so is transported and stored by the host iron-binding proteins transferrin and ferritin, respectively.

*M. tuberculosis*, like other pathogenic bacteria, however, have evolved complex mechanisms to scavenge host iron even intra-cellularly from macrophages which are considered the first line of defense following infection. Like some other microorganisms, *M. tuberculosis* scavenges iron through the production and secretion of iron chelating siderophores.

The present inventors have discovered that extra-cellular ferric iron accumulates within foci of necrosis in primary lesions coincident with the development of dystrophic calcification. The accumulation of iron within primary lesions was preceded by the expression of transferrin receptors (CD71) and H ferritin by macrophages, which was ameliorated by BCG vaccination. Both in vivo and in vitro data show that iron metabolism by macrophages is reflective of activation status and at least in part, determines resistance to *M. tuberculosis* infection.

Some aspects of the invention thus provide a vaccine that comprises at least a portion of an HIF inducing compound that is produced by the microorganism, a precursor of the HIF inducing compound, or a combination thereof. Similar to using only an epitope of microorganism's protein in vaccine, some embodiments of the invention use only a portion of the HIF inducing compound and/or a precursor thereof that is recognized by the immune system of the subject. One skilled in the art can readily determine the necessary portion of any compound for immune response by, for example, by isolating the antibody produced by the subject's immune system and systematically testing against various portions of the compound or by modeling the recognition site (e.g., binding pocket) of the antibody and the compound and determining which portion of the compound fits within the antigen recognition site of the antibody.

Microorganism (or microbe) can be any microorganism that produces an HIF inducing compound. Typically vaccine is for microorganisms that are harmful to the subject; however, it should be appreciated that the scope of the invention is not limited to such microorganisms. In general, the invention is applicable for any microorganism (e.g., bacteria, fungi, etc.) that produces an HIF inducing compound.

In some embodiments, the invention provides vaccine for microorganisms that produce siderophore(s). As stated above, a siderophore is an iron chelating compound secreted by the microorganism. It should be appreciated, however, that siderophores can also chelate other metal cations such as copper, magnesium, manganese, nickel, etc. Exemplary microorganisms that are known to produce siderophore(s) include various bacteria and fungi. Specific examples of siderophores produced by various microorganisms and the microorganisms that produce them (in parenthesis) include ferrichrome (*Ustilago sphaerogena*), enterobactin (*Escherichia coli*), mycobactin (*Mycobacterium*), enterobactin and bacillibactin (*Bacillus subtilis*), ferrioxamine B (*Streptomyces pilosus*), fusarinine C (*Fusarium roseum*), yersiniabactin (*Yersinia pestis*), vibriobactin (*Vibrio cholerae*), azotobactin (*Azotobacter vinelandii*), pseudobactin (*Pseudomonas* B 10), erythrobactin (*Saccharopolyspora erythraea*) or ornibactin (*Burkholderia cepacia*). In some embodiments, the invention provides vaccine that comprises at least a portion of a siderophore and/or a precursor thereof. Within these embodiments, in some cases the siderophore is mycobactin, carboxymycobactin, exochelins, or a combination thereof.

In one particular embodiment, the microorgansim is a bacteria. Within these embodiments, the microorganism is *Mycobacterium*. Exemplary *Mycobacterium* include *M. abscessus, M. africanum, M. agri, M. aichiense, M. alvei, M. arupense, M. asiaticum, M. aubagnense, M. aurum, M. austroafricanum, Mycobacterium avium* complex (MAC) [MAC is a group of species which are a significant cause of death in AIDS patients; species in this complex include *M. avium, M. avium* paratuberculosis, which causes Crohn's disease in humans and Johne's disease in cattle and sheep, *M. avium silvaticum*, and *M. avium* "hominissuis"], *M. boenickei, M. bohemicum, M. bolletii, M. botniense, M. bovis, M. branderi, M. brisbanense, M. brumae, M. canariasense, M. caprae, M. celatum, M. chelonae, M. chimaera, M. chitae, M. chlorophenolicum, M. chubuense, M. colombiense, M. conceptionense, M. confluentis, M. conspicuum, M. cookii, M. cosmeticum, M. diernhoferi, M. doricum, M. duvalii, M. elephantis, M. fallax, M. farcinogenes, M. flavescens, M. florentinum, M. fluoroanthenivorans, M. fortuitum, M. fortuitum* subsp. *acetamidolyticum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. hodleri, M. holsaticum, M. houstonense, M. immunogenum, M. interjectum, M. intermedium, M. intracellulare, M. kansasii, M. komossense, M. kubicae, M. kumamotonense, M. lacus, M. lentiflavum, M. leprae* (which causes leprosy), *M. lepraemurium, M. madagascariense, M. mageritense, M. malmoense, M. marinum, M. massiliense, M. microti, M. monacense, M. montefiorense, M. moriokaense, M. mucogenicum, M. murale, M. nebraskense, M. neoaurum, M. neworleansense, M. nonchromogenicum, M. novocastrense, M. obuense, M. palustre, M. parafortuitum, M. parascrofulaceum, M. parmense, M. peregrinum, M. phlei, M. phocaicum, M. pinnipedii, M. porcinum, M. poriferae, M. pseudoshottsii, M. pulveris, M. psychrotolerans, M. pyrenivorans, M. rhodesiae, M. saskatchewanense, M. scrofulaceum, M. senegalense, M. seoulense, M. septicum, M. shimoidei, M. shottsii, M. simiae, M. smegmatis, M. sphagni, M. szulgai, M. terse, M. thermoresistibile, M. tokaiense, M. triplex, M. triviale, Mycobacterium tuberculosis* complex (MTBC), [MTBC members are causative agents of human and animal tuberculosis; species in this complex include *M. tuberculosis* (the major cause of human tuberculosis), *M. bovis, M. bovis* BCG, *M. africanum, M. canetti, M. caprae, M. pinnipedii], M. tusciae, M. ulcerans* (which causes the "Buruli", or "Baimsdale, ulcer"), *M. vaccae, M. vanbaalenii, M. wolinskyi*, and *M. xenopi*. In particular embodiment of the invention, the microorganism is *M. tuberculosis*. In this particular embodiment, the vaccine can be a conventional BCG vaccine that comprises at least a portion of a HIF inducer and/or a precursor thereof.

Vaccines of the invention can further comprise a vaccine composition of a conventional vaccine such as epitope of microorganism, inactivated or attenuated microorganism, genetically modified microorganism, etc.

Compositions (e.g., vaccines) of the invention can be formulated and administered by any of the conventional methods known to one skilled in the art. For example, compositions of the invention can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, nasal inhalation via insufflation and aerosol; and intraperitoneal.

The composition can be orally administered, for example, with an inert diluent or with an assimilable edible carrier, or it can be enclosed in hard or soft shell gelatin capsules, or it can be compressed into tablets. For oral administration, the composition can be incorporated with excipient and used in the form of ingestible tablets, buccal tablets, troches, capsules, elixirs, suspensions, syrups, wafers, and the like.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the form is a capsule, it can contain, in addition to materials of the above type, a liquid carrier. Various other materials can be present as coatings or to otherwise modify the physical form. For instance, tablets, pills, or capsules can be coated with shellac, sugar or both. A syrup or elixir can contain sucrose as a sweetening agent, methyl and propylparabens a preservatives, a dye and flavoring such as cherry or orange flavor. Of course, any material used should be substantially pure and substantially non-toxic in the amounts employed. In addition, the composition can be incorporated into sustained-release preparations and formulation.

The vaccine can also be administered parenterally. Solutions of the vaccine can be prepared, for example, in water optionally suitably mixed with a surfactant such as hydroxypropylcellulose. Dispersion can also be prepared in glycerol, liquid polyethylene glycols, and mixtures thereof and in oils. Under ordinary conditions of storage and use, these preparations can contain a preservative to prevent the growth of microorganisms.

Forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

Additional objects, advantages, and novel features of this invention will become apparent to those skilled in the art upon examination of the following examples thereof, which are not intended to be limiting.

EXAMPLES

Materials and Methods

Experimental Animals

Specific pathogen-free albino Hartley-strain guinea pigs (Charles River Breeding Laboratories, Inc., Wilmington, Mass.) were housed at six per cage in Noryl® plastic cages (Allentown Caging Equipment Co., Inc.) and provided commercial guinea pig chow (Purina 5025; Overland Wholesale Supply, Brighton, Colo.) in stainless-steel feeders and tap water ad libitum. The guinea pigs were maintained in a temperature- and humidity-controlled environment and exposed to a 12-hour light/dark cycle. Each animal was randomly assigned to a vaccination treatment group. Wild-type CBA mice or INFγ KO mice were purchased from a commercial source.

Aerosol Infection

*Mycobacterium tuberculosis* H37Rv strain (TMC #102; Trudeau Institute, Saranac Lake, N.Y.) was grown in Proskauer-Beck liquid medium containing 0.05% Tween 80 to mid-log phase, aliquoted, and frozen at −80° C. until used for infection (MRL Laboratories, Colorado State University). A thawed aliquot of *M. tuberculosis* was diluted in sterile water to 106 CFU/mL for a total working stock volume of 20 mL. Guinea pigs (approximately 9 months of age) from each treatment group were aerosolized using the Madison infection chamber (University of Wisconsin Machine Shop, Madison, Wis.) with a starting volume of 15 mL of working stock. Non-infected controls were aerosolized with sterile water only.

BCG Vaccination

Guinea pigs were vaccinated with $1\times10^4$ *Mycobacterium bovis* (BCG, strain Pasteur) or mock vaccinated with saline, intra-dermally 4 weeks prior to aerosol exposure to *M. tuberculosis.*

Euthanasia and Sample Collection

At intervals of 5, 10, 15, 20, 30 and 60 days post-infection, guinea pigs were euthanized humanely by an overdose (1 mL per 0.75 kg body weight) of sodium pentobarbital (Sleepaway; Fort Dodge Laboratories Inc.) by intraperitoneal injection. Following euthanasia, the left pulmonary lobes were infused in situ with 5 mL of 4% paraformaldehyde for 48 hours and stored in 70% ethanol. At the time of processing, all tissues were embedded in paraffin, sectioned at 5 μm, and stained with hematoxylin and eosin (H&E), Pearl's Prussian blue for ferric iron, Turnball's for ferrous iron or Von Kossa's for calcium. In a separate experiment Guinea pigs were injected intraperitoneally with pimonidazole, a hypoxia marker, one and a half hour prior to euthanasia, followed by tissue processing as described above.

Human Archival Specimens

Tissue specimens were collected from patients from the National Jewish Medical and Research Center, Denver, Colo. All donors were HIV-1 and HIV-2 seronegative. The subjects did not present with any clinical symptoms of atopic disorders or parasitic/helminth infestation. Clinically active class 3 pulmonary tuberculosis was diagnosed by chest radiography and confirmed by positive acid-fast bacillus (AFB) smear or positive sputum culture (SCP). An active TB infection was diagnosed by the existence of middle or lower lung zone involvement.

Immunohistochemistry

Paraffin sections, 5-6 μm, of (i) lung and tracheobronchial lymph nodes from the experimentally infected guinea pigs, (ii) archival samples of resected lung lesions from human patients with confirmed *M. tuberculosis* infection, and (iii) mice experimentally infected with *M. tuberculosis*, collected on positively charged glass slides, were deparaffinized, rehydrated and subjected to antigen retrieval by incubation in Target Retrieval solution, pH 9.0 (DAKO, Carpentaria, Calif.) for the HIF-1 AND HO-1 labeling, and in citrate-buffer, pH 6.0 for the VEGF-stain, for 25 min at 90° C., followed by a 20 min cooling period at room temperature. The sections were then treated with 0.3% hydrogen peroxide in water for 15 min to quench endogenous peroxidase activity. Following a rinse in Tris buffered saline with 1% Tween-20 (TTBS), the slides were subjected to two blocking steps: (i) 15 min incubation with 0.15 mM. glycine in PBS, and (ii) 30 min incubation with 1% normal horse serum with a rinse in TTBS in between. The slides were then incubated with rabbit polyclonal antibody to HIF-1 (BioReagents, Golden, Colo.) or rabbit polyclonal antibody specific for VEGF (Lab Vision, Fremont, Calif.), both at a 1:100 dilution in blocking buffer, or with rabbit polyclonal antibody specific for HO-1 (Santa Cruz Biotechnology, Inc., Santa Cruz, Calif.) at 1:400 dilution, followed by several rinses in TBSS. This was followed by 30 min incubation with biotinylated goat-anti rabbit-IgG (Vector Laboratories) and visualization of bound antibody by the ABC-method (Vectastain; Vector Laboratories) and diaminobenzidine or AEC substrate (Dako; Carpentaria, Calif.). The sections were counterstained with Meyer's hematoxylene (Scytek Laboratories; Logan, Utah), mounted with coverslips, and examined on an Olympus BX41 light microscope. Photomicrographs were acquired with an Olympus Q-Color 3 camera and associated computer software. The number of positive cells were scored as follows: 0=no positive cells apparent, 1=scattered, rare positive cells, 2=small numbers, often clustered, of positive cells, 3=moderate numbers of positive cells, 4=large numbers of positive cells. For visualization of the hypoxia probe, pimonidazole, sections from the formalin-fixed tissues were de-paraffinized and subjected to antigen retrieval using proteinase K (DAKO) for 30 min at 37-40° C. This was followed by inactivation of endogenous peroxidase activity with 0.3% hydrogen peroxide for 5 min, blocking of non-specific binding with normal horse-serum, followed by application of the primary antibody, Hydroxyprobe-1 monoclonal antibody (Chemicon Int., Temecula, Calif.) for 40 min at room temperature. Following thorough washing the biotinylated secondary antibody was applied, followed by streptavidin-peroxidase. Bound antibody was visualized with DAB or AEC chromagen.

Mycobactin

Iron saturated mycobactin J was purchased from Allied Monitor (Fayette, Mo.). Iron was removed and mycobactin purified by initially reconstituting the lyophilized solution of crude $Fe^{3+}$-mycobactin J complex in $CHCl_3$ and 4N HCl. The suspension was stirred for 30 min. The water phase was separated and 4N HCl was added. After being stirred for 30 min, water phase was removed; this process was conducted three times to provide clear color solution. The $CHCl_3$ phase was dried over $Na_2SO_4$, and concentrated in vacuo. Purification by $SiO_2$ ($CHCl_3$:MeOH=20:1) gave $Fe^{3+}$-free mycobactin J. The preparation was determined to be greater than 94% pure by NMR spectroscopy. Crude preparations of mycobactin J (50 mgs) yielded 9.8 mg following iron removal and purification. The iron binding capacity of iron saturated and $Fe^{3+}$-free preparations were determined by the ferrozine method (Eagle Diagnostics, Desoto, Tex.). The $Fe^{3+}$-saturated mycobactin had the iron binding capacity of 0 μmol/L and the $Fe^{3+}$-free preparation bound 66.7 μmol/L. The iron binding capacity of desferrioxamine was determined.

Tissue Analyses

Grossly visible primary lung lesions for chemical analysis were dissected from paraformaldehyde fixed lungs of BCG- or sham-vaccinated guinea pigs. Random sections of paraformaldehyde fixed lung from non-infected animals were used as negative controls. Tissues were dried overnight in a drying oven at about 85° C., weighed, and ashed overnight in a muffle furnace at approximately 600° C. The ashed samples were allowed to cool, and then dissolved in nitric acid. The solutions were sonicated to complete dissolution. The resulting acid solution was diluted with deionized water for copper, iron and zinc analyses, and diluted with 5% lanthanum for calcium and magnesium analyses. Calcium, copper, iron, magnesium and zinc concentrations were determined via flame atomic absorption spectrophotometry. The concentration of phosphorus was determined by reacting the acid solution with ammonium molybdate and measuring the absorbencies using UV/VIS spectrophotometry. All tissue concentrations were reported as parts per million (PPM) on a dry weight basis.

In Vitro Exposure of Guinea Pig Alveolar Macrophages and Human Myelomonocytic Cells to Iron Chelators.

Alveolar macrophages were procured from naïve and BCG-vaccinated guinea pigs by lavage of the lungs in situ immediately following euthanasia. The isolated cells were subjected to Percoll gradient centrifugation (BO & Babiuk) to remove contaminating epithelial cells, neutrophils and erythrocytes. The cells were subsequently incubated overnight in chamber slides (Nunc) in RPMI medium with 10% fetal bovine serum (FBS) and antibiotics to allow the cells to adhere. THP-1 and HL60 cells, obtained from the ATCC (Rockville, Md.), were maintained in suspension in RPMI/10% FBS. The various cell types were washed thoroughly in Hank's balanced salt solution (HBSS) before incubation in HBSS without or with mycobactin or desferroxamine at various concentrations and for various length of time (see result section). At the end of the incubation time the spend media were collected and stored at −70° C. for later assay for IL-8 and TNF-α. The cells were then either spotted onto Teflon coated slides for immunolabelling for HIF-1α or HO-1 (see above) or were subjected to differential lysis to procure cytoplasmic and nuclear proteins, respectively. The protein samples were separated on 10% SDS-polyacrylamide gels and blotted onto nitrocellulose membranes. The membranes were subsequently incubated with the HIF-1α or HO-1 specific antibodies, and binding visualized by chemiluminescence.

Cytokine Assays

IL-8 produced by the human myeloid cell lines HL-60 and THP-1 or by guinea pig alveolar macrophages in response to various stimuli (see above) was measured using the DuoSet® ELISA kits from R&D Systems (cat. no. DY208). Briefly, microplates were coated with the capture antibody specific human IL-8 by incubation overnight. Following removal of unbound antibody the plates were blocked, followed by addition of sample or standard and incubation for 2 hours at room temperature. Following thorough washing biotinylated secondary antibody was applied. Visualization of captured cytokine was done by applying streptavidin-HRP complex followed by enzyme substrate, and measurement of color development on a microplate reader.

TNF-α was quantitated using the L929-cytotoxicity assay and TGFβ1 assay was done by ELISA.

Statistics

Results are expressed as mean±standard deviation (SD). A statistical software package (Graphpad® Prizim 4.02, San Diego, Calif.) was used for data analysis and graphics. Differences between groups were compared by two-way analysis of variance (ANOVA). Bonferroni post-test was used to assess differences within and between treatment groups. The values of $P \leq 0.05$, $P \leq 0.001$ were considered significant.

Results

In Vivo Expression of HIF-1α, HO-1 and VEGF in Lungs and Lymph Nodes of M. Tuberculosis Infected Guinea Pigs.

As early as five days post challenge many alveolar and interstitial macrophages in the lungs of non-vaccinated guinea pigs aerosol-challenged with M. tuberculosis expressed HIF-1α cytoplasmically accompanied by nuclear translocation. The number of HIF-1α positive cells, mostly macrophages, increased steadily over time, with the majority of positive cells localizing in the developing granulomas. Expression of HIF-1α in the corresponding tracheobronchial lymph nodes followed a similar pattern. Notably, the expression of HIF-1α preceded the development of lesion hypoxia, and was at all time points more widespread than the tissue hypoxia as detected with the hydroxy-probe. The expression of HO-1 in the macrophages, both alveolar macrophages and infiltrating macrophages in the developing granulomas, closely followed the pattern of HIF-1α expression and its nuclear translocation.

Similar kinetics and distribution of HIF-1α and HO-1 expressing cells were found in the BCG-vaccinated animals, but at most time points and notably later time pints, there was overall fewer positive cells in the BCG-vaccinated, M. tuberculosis challenged animals compared to non-vaccinated animals.

While there was apparent correlation in kinetics and distribution of VEGF-expression compared to HIF-1α expression in both non-vaccinated and BCG-vaccinated guinea pigs, the overall number of cells expression VEGF was at any one time point greater than the number of cells displaying HIF-1α nuclear translocation, possibly suggesting that mechanisms other than HIF-1α transcription regulation are involved in up-regulation and expression of VEGF. Notably, at the earliest time point studied, 5 days p.i., many alveolar macrophages expressed VEGF. At various time points there was also expression of VEGF in bronchiolar epithelial cells, and in some animals the distribution of VEGF-positive cells was concentrated in areas immediately adjacent to medium sized pulmonary vessels.

Approximately 10-20% of alveolar macrophages, retrieved by lung-1α vage from non-infected, non-vaccinated or BCG-vaccinated guinea pigs and purified by Percoll-gradient centrifugation, expressed cytoplasmic HIF-1α but nuclear translocation was not noted and HO-1 expression was undetectable.

HIF-1α and HO-1 Expression in Mycobacterial Lesions in Humans

To access the relevance of the findings in the guinea pig model to that of human mycobacterial infections, archival samples from lung of human mycobacterioses were immunolabeled for HIF-1α, HO-1 and VEGF. While these samples did not allow for assessment of the kinetics of expression in humans, and in most cases represented late-stage cavitary or severely fibrotic lesions, the expression of HIF-1α and HO-1 was largely restricted to infiltrating macrophages, including multinucleated giant cells in the granulomas and alveolar macrophages in patent alveoli, the latter suggesting that tissue hypoxia may not be a pre-requisite for HIF-1α upregulation and nuclear translocation.

HIF-1α and HO-1 Expression in Mycobacterial Lesions in Mice

Mice challenged with *M. tuberculosis* did not, with the notable exception of IFN-γ knock-out mice, develop classical granulomas, as seen in humans, non-human primates and guinea pigs. Rather, lesions were composed of more or less random accumulations of macrophages, neutrophils and lymphocytes, including many B cells and plasma cells at later stages of the infection, in the alveoli and interstitiae, lacking a distinct organization. It has been shown that hypoxia is not a characteristic of the lesions in mice. Nevertheless, immunolabelling for HIF-1α and HO-1 demonstrated very pronounced expression of both molecules in murine TB-lesions, as well as in alveolar and interstitial macrophages of the surrounding parenchyma of these animals.

Mycobactin Induction of HIF-1α in Macrophages in Vitro

Employing human myelomonocytic cell lines (THP-1 and HL-60 cells) and guinea pig alveolar macrophages, procured by lavage and purified by gradient centrifugation, it was found that the naturally occurring iron chelator from *M. avium* ssp. paratuberculosis, mycobactin J and the drug desferroxamine induced accumulation of cytoplasmic HIF-1α in a dose-dependent manner followed by nuclear translocation in a subset of the cells. Mycobactin appeared to be more potent for this effect compared to desferroxamine on a molar level (1-5 μM mycobactin versus 10-100 μM desferroxamine), but the kinetics of induction was comparable for the two agents with maximum detectable effect at 16-24 hours of drug-exposure. The nuclear translocation of HIF-1α resulted in induction of IL-8 secretion, an effect that was enhanced by differentiation of the human cells to more mature macrophages with PMA. In contrast, induction of TNF-α and TGFβ1 production under these culture conditions, following HIF-1α upregulation and nuclear translocation, appeared to be minimal.

Discussion

The morphogenesis of the primary lung lesions of naive guinea pigs experimentally infected with *M. tuberculosis* by low-dose aerosol notably differed from primary lesions in BCG vaccinated guinea pigs. Primary lung lesions in naive guinea pigs showed characteristic areas of central necrosis that progressed to dystrophic calcification by 8 weeks post-infection. The primary lung lesions in BCG-vaccinated guinea pigs rarely developed central necrosis and failed to develop dystrophic calcification even out to 8 weeks post-infection, but were present as a mixture of predominately lymphocytes and fewer macrophages. By routine H&E staining, calcified debris was characterized by coarsely granular basophilic stippling, either extra-cellular or intra-cellular. Cells that were in the early stages of calcification had basophilic cytoplasm but retained nuclear morphology. As the lesions progressed, extra-cellular and intra-cellular calcification consolidated to form discrete calcified nodules.

The stains Pearl's Prussian blue for ferric iron, Turnball's stain for ferrous iron and Von Kossa's stain for calcium were used to compare the accumulation of iron and calcium within the primary lung lesions of sham-vaccinated and BCG-vaccinated guinea pigs prior to low dose aerosol challenge. At 4 weeks post-infection in sham-vaccinated guinea pigs, neither ferric iron nor calcium was evident within early primary lesions with acute inflammation and central necrosis.

However, the accumulation of intra- and extra-cellular ferric iron and calcium occurred between 4 and 8 weeks post-infection. Primary lesions of sham-vaccinated guinea pigs at 8 weeks post-infection had punctuate extra-cellular deposits of ferric iron and calcium mixed with necrotic debris. Dead or degenerate cells within necrotic lesions had diffuse cytoplasmic calcification, often with intact cytoplasmic margins.

As lesions progressed, ferric iron, but not ferrous iron (data not shown), accumulated intra-cellularly in macrophages within the cell rich periphery of primary lesions or was incorporated into central foci of dystrophic calcification and concentrated at the periphery of the calcified lesion at the interface with the acellular but non-mineralized zone of the lesion. More organized lesions had diffuse calcification of necrotic debris that was well delineated from the cellular and acellular zones of the lesion. In contrast, the primary lesions in BCG vaccinated animals had neither intra-cellular nor extracellular iron accumulation at 4 weeks post infection. Only intra-cellular ferric iron was evident at 8 weeks post-infection with no evidence of extra-cellular iron accumulation.

The lack of extracellular iron accumulation correlated with the lack of central necrosis and mineralization. The difference in the progressive accumulation of iron and calcium seen histologically in lesions from *M. tuberculosis* infected guinea pigs was confirmed by quantifying total iron and calcium concentrations in isolated primary lung lesions. At 4 weeks post-infection, the concentration of calcium in sham- and BCG-vaccinated animals was not different from controls, but concentrations increased significantly in sham-vaccinated animals by 8 weeks post-infection. Total iron concentrations in primary lesions from BCG-vaccinated animals were increased above sham-vaccinated and normal controls at 4 weeks post-infection, but decreased to control levels by 8 weeks post-infection.

In contrast, total iron concentrations increased progressively in primary lesions from sham-vaccinated animals to levels that were significantly higher than lesions from BCG-vaccinated or non-infected controls. Dystrophic calcification consists predominately of calcium phosphate, but includes a complex of elements. To determine what effect BCG vaccination had on other components of mineralized lesions, primary lung lesions from *M. tuberculosis* infected guinea pigs were analyzed for phosphorus, magnesium, copper and zinc. Similar to total iron concentrations, phosphorus and magnesium concentrations in isolated primary lesions from sham-vaccinated animals increased significantly above those of non-infected controls and those from BCG-vaccinated animals.

Copper and zinc concentrations were also measured in primary lesions but did not vary significantly over time between sham-vaccinated, BCG vaccinated or non-infected controls. It is believed that limiting intracellular iron availability is one mechanism by which activated macrophages control the growth of *M. tuberculosis*. Immunohistochemistry was used to determine what effect BCG vaccination had on the macrophage expression of transferrin receptor (CD71) and H ferritin in vivo. Macrophages within lesions were identified for the presence of lysozyme by immunohistochemistry (data not shown). Macrophage H ferritin expression increased from 4 to 8 weeks post-infection within primary lung lesions from sham-vaccinated guinea pigs infected with *M. tuberculosis*. Ferritin accumulated intra-cellularly in macrophages that encircled the necrotic centers of the lesion. The expression of H ferritin in lesions from BCG-vaccinated animals was delayed such that compared to sham-vaccinated animals it was significantly less at 4 weeks post-infection, but by 8 weeks post-infection, the total number of cells expressing H ferritin in the BCG- and sham-vaccinated animals was similar.

Macrophages encircling necrotic centers in sham-vaccinated guinea pigs expressed transferrin receptor in a pattern similar to that of H ferritin. In BCG-vaccinated animals where necrosis was rare, transferrin receptor expression was more diffusely distributed within the primary lesions. In the early stages of infection, the total expression of macrophage transferrin receptor was significantly increased in BCG-vaccinated animals compared to sham-vaccinated controls. Ferritin expression in primary lesions, first increased in sham-vaccinated animals at 20 days post-infection and 30 days post-infection in BCG-vaccinated animals and were not significantly different at 60 days post-infection The significant increase in expression in sham-vaccinated animals parallels the peak of necrosis seen histologically. The variable expression of H ferritin seen in BCG-vaccinated animals reflected occasional primary lesions that showed non-progressive necrosis. The expression of transferrin receptor was seen in primary lesions as early as 5 days post-infection. The increase in the number of total cells expressing transferrin receptor was progressive in both BCG- and sham-vaccinated animals. While BCG-vaccinated animals had the greatest expression early following aerosol challenge, differences compared to sham-vaccinated controls were not statistically different. Despite the amelioration of transferrin receptor expression within individual primary lesions in BCG-vaccinated animals, the mean scores between BCG- and sham-vaccinated animals were not statistically different at days 30 and 60 post-infection. Ferritin and CD71 expression in mediastinal and peribronchial lymph nodes paralleled that seen in the lungs (data not shown).

The present inventors have discovered that HIF-1α and HO-1 were expressed in the lesions of experimental tuberculosis in guinea pigs, mice and biopsy specimens from humans with naturally occurring M. tuberculosis infection. Lesion hypoxia is a feature of advanced cases of human tuberculosis and is believed to be associated with the primary lesions in immunologically naïve guinea pigs experimentally infected with M. tuberculosis by low dose aerosol. It was observed that HIF-1α expression occurred early following experimental infection of guinea pigs and in the mouse model of tuberculosis that fails to develop lesion hypoxia. HIF-1α as well as the down stream regulated gene product HO-1 were highly expressed as early as 30 days post challenge. The significance of these findings is that while hypoxia is the primary stimulus of cellular HIF-1α expression and function, it is believed that non-oxygen dependent mechanisms also account for the expression of this host transcription factor in tuberculosis. A number of host growth factors and cytokines have been shown to up regulate HIF-1α as well as some bacterial products such as LPS and the iron chelating siderophore mycobactin. Without being bound by any theory, it is believed that in the course of infection, bacteria and bacterial products induce the expression of HIF-1α in the absence of low tissue oxygen concentration thus mimicking hypoxia in a non-oxygen dependent fashion.

Mycobactins are the highly lipid soluble iron binding siderophores of pathogenic mycobacteria. Mycobactin is believed to be primarily cell associated in viable mycobacteria and functions as a molecule that temporarily stores iron prior to intracellular transport. The structurally similar mycobacterial siderophore carboxymycobactin is water soluble and functions to bind and transport host acquired iron to the bacterial containing phagasome. Mycobactin was shown to be significantly more potent at inducing HIF-1α in THP-1 cells in vitro despite having a lower iron binding capacity than desferrioxamine when compared on a molar equivalent. The difference in biologic activity is believed to be due to the greater lipid solubility of mycobactin. It is also possible that the induction of HIF-1α is independent of the iron chelating activity of mycobactin. One of the possible mechanism of HIF-1 induction by iron chelation is by stabilizing HIF-1α directly as the protein itself has iron as a structural cofactor. HIF-1α stabilization by both desferrioxamine and mycobactin is possibly through the iron chelating activity resulting in sequestration and reduction of the labile cytoplasmic iron pool.

The expression of HIF-1α with nuclear translocation in lung and lymph node cells as early as 5 days, prior to the development of extensive inflammatory lesions, is consistent with an oxygen independent mechanism of HIF-1α induction. In non-vaccinated guinea pigs where the primary lesions of both lung and lymph node develop extensive lesion necrosis, the majority of IHC positive cells are concentrated in the inflammatory zone adjacent to central lesion necrosis. The lack of staining within the necrotic zone is believed to be due to the lack of viable cells and normal tissue architecture. This pattern of HIF-1α expression correlates with the zone of hypoxia revealed by piminidazole staining Vaccination with M. bovis BCG prior to challenge significantly abrogated the number of HIF-1α positive cells in the lung but lymph node expression was not different from non-vaccinated control animals. A similar pattern of staining was seen when nuclear staining among treatment groups was compared. This observation supports the belief that the lymphatic drainage in the both the lung and the lymph node represents a microenvironment that favors the growth and virulence of M. tuberculosis. These data suggests that one factor that contributes to the increased virulence of M. tuberculosis in the lymph reflected by relatively rapid growth and tissue destruction may be due to hypoxia developing sooner compared to the lung. Furthermore, while M. bovis BCG vaccination abrogates lesion necrosis and delays the progression of inflammation in the lymph node, progressive granulomatous inflammation ultimately effaces the normal lymph node architecture. Previously the present inventors have shown that the pulmonary lymphatics where primary lesions develop following aerosol challenge, represents a microenvironment that is unique from the pulmonary parenchyma.

In experimental tuberculosis in guinea pigs and naturally occurring infection in humans, M. tuberculosis persists in lesions that have zones of necrosis and local hypoxia. These data are further supported by the current study. Mice are the most widely used animal model of human tuberculosis but have the distinct disadvantage of developing lesions that fail to become hypoxic. Despite the lack of lesion hypoxia, lesions as early as 30 days post-challenge express HIF-1α and HO-1 indicating an oxygen-independent expression of HIF-1α. Moreover, particularly in IFN-γ KO mice, alveolar macrophages within normal appearing alveoli peripheral to inflammatory lesions express HIF-1α similar to those seen in biopsy specimens from humans with naturally occurring tuberculosis.

Iron metabolism by all living organisms is closely linked to cell respiration. Iron is a critical cofactor for both heme and non-heme proteins but is also important for other biochemical functions such as DNA synthesis. Because of the limited ability to store iron, some microorganisms such as M. tuberculosis has evolved an elaborate system to acquire host iron through the iron chelating activity of siderophores, e.g., mycobactin and carboxymycobactin. Iron is insoluble at physiologic pH and is tightly bound to several intracellular or circulating host iron binding proteins. Because of a higher binding capacity, siderphores can acquire and sequester intracellular and extracelluar iron to be used for intracellular growth and replication of *M. tuberculosis*.

In some studies, the temporal relationship between the accumulation of extra-cellular iron and calcification in the primary lesions of guinea pigs infected with *M. tuberculosis* was examined by exploiting the morphologic differences between the primary lesions in BCG-vaccinated and non-vaccinated guinea pigs. Such study was used, among others, to better understand the mechanisms of action of BCG in vivo and the pathogenesis of dystrophic calcification of primary lesions. The visualization of calcified lesions in the lungs and lymph nodes of humans by radiography has been recognized as an important criterion in the clinical diagnosis of tuberculosis. Primary lesions characterized by calcification are resistant to treatment with first line anti-tuberculosis drugs and may therefore contribute to the development of multi-drug resistant strains of *M. tuberculosis*.

The accumulation of iron within the primary lesions of *M. tuberculosis* infected guinea pigs is consistent with the observation that the macrophage is central to the pathogenesis of tuberculosis and plays an important role in normal host iron metabolism. However, observation of accumulation of extra-cellular ferric iron within the foci of necrosis that coincided with the development of dystrophic calcification was surprising and unexpected.

Ferric iron was incorporated into the mineralized matrix with a restricted peripheral distribution, a region that may be available for scavenging by persistent, viable bacilli in the non-mineralized, acellular margins of the primary lesions. Given that extracellular, but not intra-cellular, iron can serve as an initiator of dystrophic calcification, it is believed that iron is not only important in *M. tuberculosis* virulence but is believed to play a role in the pathogenesis of primary lesions of tuberculosis. Iron not only initiate calcification but the initial tissue necrosis is believed to be mediated in part by free iron which is damaging to cells, e.g., by catalyzing the generation of reactive oxygen intermediates such as highly toxic hydroxyl radicals.

Byproducts of oxygen free radical damage were detectable in the serum of patients with active tuberculosis. Applying special stains to histologic sections showed accumulations and distribution of both iron and calcium to be localized within lesions and allowed visualization BCG vaccination effect, prior to aerosol challenge, had on lesion morphogenesis. The analysis of isolated primary lesions for iron and other elements allowed quantification of the chemical composition of representative lesions and to confirm the observations made histologically. The marked increase in the calcium concentration between days 30 and 60 in the sham- and saline-vaccinated animals infected with *M. tuberculosis* was consistent with the presence of dystrophic calcification in lesions as seen with routine H&E and the Von Kossa's stain for calcium. There were significant differences in the range of calcium concentrations in randomly selected lesions of non-vaccinated animals which reflects the heterogeneity in the amount of calcification in lesions found within and between individuals. Compared to non-vaccinated animals, BCG vaccination significantly reduced measurable calcium concentrations in isolated lesions, to levels that were only modestly elevated compared to lung parenchyma of non-infected controls.

Dystrophic calcification is a complex of ions that is composed primarily of calcium and phosphorus as calcium phosphate. The increase in phosphorus in isolated primary lesions from *M. tuberculosis* infected guinea pigs sham-vaccinated with saline paralleled the increase in calcium. BCG vaccination prior to infection prevented phosphorus accumulation in isolated lesions. Additional ions are incorporated into the mineralized matrix depending on the extra-cellular concentration and the presence or absence of endogenous inhibitors of calcification.

Magnesium, like iron, is required for intra-cellular growth of *M. tuberculosis*. Magnesium was incorporated into primary lesions and had a similar pattern of accumulation and response to BCG vaccination as calcium, phosphorus and iron. Notably, copper and zinc were present in isolated primary lesions but showed no significant changes regardless of the vaccination status of *M. tuberculosis* infected animals. Zinc and copper, like iron, are essential nutrients for all organisms as they serve as catalytic or structural cofactors for many different proteins. Zinc-dependent proteins are typically found in the cytoplasm and within many organelles of the eukaryotic cell and are a cofactor for metalloenzymes that are thought to play a role in the pathogenesis of tuberculosis. Copper, in particular, is a cofactor for lysyl oxidase, an amine oxidase that is responsible for lysine-derived cross links in extra-cellular matrix proteins such as collagen and elastin. The formation of a fibrous capsule rich in collagen is a major component of the granuloma of tuberculosis and copper levels is expected to parallel the increase in collagen in primary lesions in non-vaccinated animals, particularly by 60 days post-infection. Surprisingly and unexpectedly, the opposite was true, in that only BCG-vaccinated animals showed slight increase in copper within primary lesions. Nutritional deficiencies in copper and zinc have been implicated in the increased susceptibility to infection in humans to both HIV and *M. tuberculosis*.

Iron is a cofactor for numerous heme and non-heme proteins that are involved in metabolic functions that are common to all living organisms. *M. tuberculosis* like other pathogenic bacteria has evolved complex mechanisms to acquire host iron which is limited in vivo even under normal physiologic conditions. The accumulation of ferric iron but not ferrous iron by *M. tuberculosis* coincided with the appearance of extra-cellular calcium visualized in specially stained tissue sections and total iron concentrations in isolated primary lesions. The deposition of extra-cellular ferric iron had a pattern similar to extra-cellular calcification prior to organization into fully calcified foci. These observations show that like cellular phospholipids, iron serves as an initiator of dystrophic calcification in the guinea pig model of tuberculosis.

The regulation of iron metabolism by macrophages is closely linked to the expression and internalization of transferrin bound iron to surface expressed transferrin receptors. Once internalized, iron dissociates from transferrin within the acidified phagolysosome and transferrin is often recycled to the cell surface. It is believed that *M. tuberculosis* acquires host iron within the phagosome by the secretion and binding of iron chelating-siderophores at have a higher binding capacity for iron than transferrin.

Activation of macrophages with IFN-γ prevents the accumulation of iron within the phagosome and down regulates the expression of surface bound transferrin. The increased expression of macrophage transferrin receptor expression in vivo is consistent with the phenomenon of alternative macrophage activation induced by exposure of macrophages to IL-4 in vitro. In addition, it has been shown that BCG vaccination of guinea pigs results in a notable decrease in the expression of host ferritin levels. Collectively, these data indicate that the protective effect of BCG vaccination is in part due to classical macrophage activation and the stimulation of Th1 driven cellular immune response, in contrast to alternatively activated macrophages dominated by Th2 cellular response in the non-vaccinated animal.

The present inventors have observed that ferritin expression was closely tied to the presence of lesion necrosis. Ferritin is a ubiquitous protein that is expressed in essentially all cells of the body. Ferritin has a complex structure made up of two different subunits designated heavy and light chain. Because of its complex structure, ferritin has a high capacity to store free iron by oxidizing ferrous to ferric iron and thus functions as an anti-oxidant by reducing the availability of intracellular free ferrous iron. Ferrous iron is highly reactive with oxygen and can participate in the generation of free radicals through the Fenton reaction. The heavy chain of ferritin has ferroxidase activity and therefore the anti-oxidant activity of ferritin is attributed to the heavy chain subunit. While free radical generation was not directly measured, the up-regulation of ferritin heavy chain that was regularly associated with foci of necrosis is consistent with a protective host in response to the presence of reactive ferrous iron. Interestingly, ferrous iron was not detected routinely in lesions using the Turnball's stain which may be a function of host protein binding or a lack of stain sensitivity on paraformaldehyde fixed tissues. The close association between H ferritin expression and the presence of necrosis suggests that H ferritin expression may be useful as a biomarker with prognostic or predictive value in determining the clinical outcome of tuberculosis.

Since iron toxicity is detrimental to both host macrophages and the tubercle bacillus, yet each has a strict nutritional requirement for iron, it is believed that the successful acquisition and sequestration of iron is an important determinant in the outcome of *M. tuberculosis* infection. The lack of necrosis and dystrophic calcification in lung lesions of guinea pigs vaccinated with BCG parallels the amelioration of iron accumulation, transferrin receptor and H ferritin expression by macrophages in vivo. Iron metabolism is influenced by immunopotentiation and is therefore a factor in tuberculosis vaccines and combination drug treatments.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. An immunogenic composition effective to inhibit a mycobacterium infection caused by *Mycobacterium tuberculosis* or *Mycobacterium bovis* comprising an isolated siderophore that is produced by said *mycobacterium*, said siderophore being effective to activate hypoxia inducing factor (HIF) in a sterile aqueous solution or dispersion or as sterile powder for extemporaneous preparation of sterile injectable solutions or dispersions wherein said siderophore is selected from the group consisting of mycobactin, carboxymycobactin, and exochelin.

2. The composition of claim 1, wherein said *mycobacterium* is *Mycobacterium tuberculosis* and said siderophore is naturally occurring.

3. The composition of claim 1, wherein said siderophore is recognized by the immune system of said subject.

4. The composition of claim 1, wherein said siderophore is mycobactin.

5. The composition of claim 1 wherein said *mycobacterium* is *Mycobacterium tuberculosis* and said composition further comprises an attenuated or inactivated *Mycobacterium tuberculosis*.

6. The composition of claim 3 wherein said *mycobacterium* is *Mycobacterium tuberculosis*, said siderophore is mycobactin and said composition further comprises an attenuated or inactivated *Mycobacterium tuberculosis*.

7. An immunogenic composition for inhibition of *Mycobacterium tuberculosis* infection for administration to a subject in need thereof, said composition comprising isolated, naturally occurring mycobactin, carboxymycobactin or exochelin produced by said *M. tuberculosis*, in a sterile aqueous solution or dispersion or as sterile powder for extemporaneous preparation of sterile injectable solutions or dispersions, said mycobactin, carboxymycobactin or exochelin being recognized by the immune system of said subject.

8. The composition of claim 7 wherein said *mycobacterium* is *Mycobacterium tuberculosis*, said siderophore is mycobactin and said composition further comprises an attenuated or inactivated *Mycobacterium tuberculosis*.

9. A method for stimulating an immune response against *Mycobacterium tuberculosis* in a subject comprising administering the composition of claim 1.

10. The method of claim 9, wherein the composition further comprises an epitope of *Mycobacterium tuberculosis*.

11. The method of claim 9, wherein the composition further comprises an attenuated or inactivated *Mycobacterium tuberculosis*.

* * * * *